United States Patent
Geistert et al.

(10) Patent No.: US 8,676,352 B2
(45) Date of Patent: Mar. 18, 2014

(54) IMPLANTABLE ELECTRODE LINE

(75) Inventors: Wolfgang Geistert, Rheinfelden (DE); Ulrich Franke, Berlin (DE)

(73) Assignee: Biotronik CRM Patent AG (CH)

( * ) Notice: Subject to any disclaimer, the term of this patent is extended or adjusted under 35 U.S.C. 154(b) by 1172 days.

(21) Appl. No.: 12/469,722

(22) Filed: May 21, 2009

(65) Prior Publication Data
US 2010/0131036 A1 May 27, 2010

(30) Foreign Application Priority Data
May 23, 2008 (DE) .......... 10 2008 024 924

(51) Int. Cl.
*A61N 1/00* (2006.01)
(52) U.S. Cl.
USPC .......................................... 607/126
(58) Field of Classification Search
USPC ................................. 607/126–128
See application file for complete search history.

(56) References Cited

U.S. PATENT DOCUMENTS

| | | | |
|---|---|---|---|
| 4,582,069 A | 4/1986 | McArthur | |
| 4,913,164 A | 4/1990 | Greene | |
| 4,957,118 A * | 9/1990 | Erlebacher | 607/128 |
| 5,238,007 A | 8/1993 | Giele et al. | |
| 5,259,395 A * | 11/1993 | Li | 607/131 |
| 6,477,423 B1 | 11/2002 | Jenkins | |
| 7,187,983 B2 * | 3/2007 | Dahlberg et al. | 607/128 |
| 2007/0021812 A1 | 1/2007 | Manning et al. | |
| 2007/0043414 A1 | 2/2007 | Fiefer | |
| 2007/0073351 A1 | 3/2007 | Zielinski | |

FOREIGN PATENT DOCUMENTS

| | | |
|---|---|---|
| DE | 696 27 790 T2 | 3/2004 |
| EP | 0 546 414 A1 | 6/1993 |
| WO | WO 2007/022180 A1 | 2/2007 |

OTHER PUBLICATIONS

European Search Report, EP 09 15 8895, Aug. 18, 2009.

\* cited by examiner

*Primary Examiner* — Christopher D Koharski
*Assistant Examiner* — Roland Dinga
(74) *Attorney, Agent, or Firm* — Craig A. Fieschko, Esq.; DeWitt Ross & Stevens S.C.

(57) ABSTRACT

A device for fastening permanently or temporarily implantable medical devices includes a main body (1) having a first end (1a) and a second end (1b), a flexible and extensible body section (2) therebetween, and a first inflexible and inextensible body support (3) which is fixedly attached to the body section (2) at the second end (1b) of the main body (1), whereby the extensible section (2) can be converted from an unextended state to an extended state in which it is lengthened in comparison with the unextended state. At least one first flexible finger-shaped anchor (4) protrudes away from the main body (1) and is attached to the first body support (3) at an anchor mount (4a). At least one first flexible retraction device (5) is provided for retraction of a respective first anchoring means (4), wherein the retraction device (5) is connected to the body section (2) and to the anchor (4). On conversion of the body section (2) from the unextended state to the extended state, the retraction device (5) does not expand, so that the respective anchors (4) are moved in the direction of the main body (1).

23 Claims, 4 Drawing Sheets ed one flexible first retraction device for retracting a respective first anchoring means is also included. The retraction device is fixedly connected to the flexible and extensible section of the main body and to the respective first anchoring means at a body fastening location.

IMPLANTABLE ELECTRODE LINE

FIELD OF THE INVENTION

The invention relates to a fastening device for affixing permanently or temporarily implantable medical devices, the fastening device having a main body, at least anchoring means (e.g., a flexible finger-shaped anchor), and at least one flexible inextensible retraction device for retracting a respective anchoring means.

In another aspect, the invention relates to an electrode line having a shaft and a fastening device for affixing permanently or temporarily implantable medical devices.

In addition, the invention relates to a system for converting an extensible section of a fastening device or electrode line between an unextended state and an extended state which is lengthened in comparison with the unextended state.

And finally, the invention relates to a method for moving the at least one anchoring means of the fastening device or electrode in the direction of a main body.

BACKGROUND OF THE INVENTION

Electrode lines for implantable medical devices are known in the art. For example, U.S. Pat. No. 4,913,164 describes unfoldable passive anchoring devices which have a device fixedly connected to a guide wire for retracting anchoring tines. By inducing movement in the guide wire, the tines can be folded up to facilitate insertion. U.S. Pat. No. 4,957,118 describes similar devices for retracting the tines of an electrode line. These devices have the disadvantage of complex technical structure, making production difficult. There are also serious disadvantages from the standpoint of reliability, manufacturability and production.

To supply accurate measurement results or to prevent harmful effects on the body, permanently or temporarily implantable medical devices must necessarily be affixed in a human or animal body so that their position remains stable. It is a major challenge to position such a device at the proper location in a body. For example, after implanting a measurement sensor, it may be found that the implantation site is unsuitable for providing accurate measurement results. The implant must then be repositioned at a more suitable location.

Repositioning or explantation of permanently or temporarily implantable medical devices has proven to be difficult. This is a particular problem with so-called passively affixable implantable medical devices because the anchoring means here protrude away from the main body of the medical device. Although these anchoring means provide good anchoring of the implantable medical device, such passive anchoring means can only be repositioned and/or explanted with great difficulty.

SUMMARY OF THE INVENTION

The present invention can allow elimination of the aforementioned disadvantages by enabling a secure, easily affixable and releasable anchoring of permanently or temporarily implantable medical devices, allowing easy repositioning and/or explantation. In addition, the aforementioned disadvantages regarding reliability, manufacturability and production can be eliminated.

The invention includes a fastening device for affixing permanently or temporarily implantable medical devices, with the fastening device including a main body having a first end and a second end, a flexible and expansible section forming the first end of the main body, and a inflexible and inextensible first body support mounted securely on the extensible section and forming the second end of the main body. At least one anchoring means (e.g., a first flexible finger-shaped anchor) protrudes away from the main body and attaches to the first body support of the main body at an anchor mount. At least one flexible first retraction device for retracting a respective first anchoring means is also included. The retraction device is fixedly connected to the flexible and extensible section of the main body and to the respective first anchoring means at a body fastening location.

The extensible section is convertible from an unextended state to an extended state which is lengthened in comparison with the unextended state, such that the body fastening location is at a distance from the anchor mount. The first retraction device does not expand (or does not significantly expand) in conversion of the extensible section from the unextended state to the extended state, so that the respective first anchoring means are moved in the direction of the main body.

The movement of the anchoring means in the direction of the main body prevents the folded anchoring means from becoming caught on body tissue and causing injuries. The anchoring means may thus remain folded up for a period of time until repositioning at a more suitable implantation site occurs. The anchoring means may then be easily unfolded again. Thus, in addition to facilitated repositioning or explantation, the invention allows easy reanchoring or attachment by the anchoring means at a more suitable implantation site.

In addition, the lengthening of the extensible section from an unextended state to an extended state can have positive effects on the release of the attachment. Due to the lengthening of the extensible section (and thus of the main body) with simultaneous folding of the anchoring means, the previously hooked anchoring means are more easily disengaged from the tissue.

For purposes of the invention, an implantable medical device can be regarded as any permanently or temporarily implanted device which can be inserted into the body to effect diagnostic or therapeutic effects. These may be electrically active implants such as cardiac pacemakers, defibrillators, cardioverters or neural stimulators. This also includes devices located in the periphery of such electrically active implants, such as electrode lines (which may lead to a body organ), intracardiac electrode lines, epicardial electrode lines, and electrodes for neural stimulation or so-called deep brain stimulation. Such devices also include sensors for measuring physiological signals, such as blood pressure or oxygen saturation sensors, which can work together with the electrically active implants mentioned above or with a transmitter/receiver for transmitting the measured data to an external device. This also includes transmitter/receiver units for transmitting data to or sending data from the body, e.g., antennas for near- or far-field telemetry. Such an implantable device may also include implants for vascular procedures, such as stents, bypasses, coils or drug depots.

The main body of the fastening device can be formed with any conceivable three-dimensional body shape. For example, a tubular shape can be chosen to cooperate with respect to the flow of the blood stream in a blood vessel. Cubic, semicircular, spherical or teardrop-shaped main bodies are also possible. The main body may have an anatomical shape adapted to the shape of the body cavity in which it is implanted.

The first retraction device is preferably affixed on the end of the first anchoring means spaced away from the main body at an anchor fastening location, such that the first retraction device—which, again, is preferably inexpansible—defines means between the body fastening location (at which the retraction device is affixed to the main body) and the anchor fastening location to prevent or reduce the elongation between the fastening locations. These means (and the first retraction device) may include steel cables or other suitable inextensible materials/elements.

It is useful if the main body of the fastening device is designed to be flexible, allowing the natural movements (e.g., peristalsis) of vessels in the body to be more readily accommodated, and possibly providing less irritation in the tissue to which the attachment device (and thus the implantable device) are attached. Such irritation can cause inflammatory changes in the tissue, and may in the worst case lead to a vascular occlusion, which can in turn lead to adverse outcomes in the case of an implantable device implanted in a blood vessel.

The extensible section of the main body is preferably designed to be flexible and extensible so that it has an unextended state and an extended state. The material properties of the flexible and extensible body section are selected so that it is possible to switch between these first and second states as often as desired, so the attachment device may be repositioned as often as desired. The extended second state is achieved when the anchoring means are in contact with the main body by cooperating with the retraction device. The anchoring means are preferably constructed so that they are prestressed and recoil into the protruding starting position on retraction into the unextended state of the extensible and flexible body section. This can be achieved, for example, by having the base of each anchoring means widened at the anchor mount, or by having the anchoring means run conically from the anchor mount in the direction of the end of the anchoring means spaced away from the main body.

Anchoring means in the sense of the present invention are considered to be, among other things, traditional and conventional tines, with or without a preferential direction of rotation, such as those used for anchoring cardiac electrode lines. DE 10 2006 014 698.0 (which is incorporated by reference herein) discloses such tines having a preferential direction of rotation.

In preferred versions of the invention, the retraction devices are designed as thin flexible fins which extend between their body fastening locations where they join the body, the anchor mounts at which their anchors join the body, and their anchor fastening locations where they join the anchor. Membranes such as those found on amphibians and reptiles are subsumed under the term "thin flexible fins." "Webbing" refers to the skin between the toes or fingers of animals that swim. It increases the efficiency of swimming movements by increasing the area of the moving feet or hands and thus allows an improved transfer of muscle force to the water. Webbing is elastic (from Wikipedia, The Free Encyclopedia, Jul. 16, 2007; http://de.wikipedia.org/wiki/Schwimmhaut [webbing]).

In preferred versions, these flexible fins or other retraction devices are attached without interruption to the body and their anchors, and extend continuously between their body fastening locations and the anchor mounts, and then extend continuously to their anchor fastening locations.

The extensible body section, the finger-like anchors or other anchoring means, and optionally the fins or other retraction devices may be made in one piece from the same extensible material. The section coated with the same extensible material from the first and/or second body supports extends around the first and/or second anchor mounts. This section is bordered on the one hand by the one end of the first and/or second body support, which is connected to the flexible section. On the other end, this section extends so far in the direction opposite the aforementioned end that the first and/or second anchor mounts are located in the coated area.

The finger-like anchors or other anchoring means are preferably designed so that the longitudinal axis of each anchoring means forms a variable angle with the main body, such that the angle is greater in the unextended state of the flexible extensible body section and is lesser in the extended state of the flexible extensible body section (in which the flexible extensible body section is also lengthened in comparison with the unextended state).

In another version of the fastening device, the main body has a second inflexible and inextensible body support fixedly attached to the first end of the main body. In this version, the fastening device preferably includes:

at least one second flexible finger-shaped anchor or other second anchoring means protruding away from the main body and attached to the second body support at an anchor mount, and at least one second flexible inextensible retraction device for retracting a respective second anchoring means, such that each retraction device is fixedly connected to the flexible and extensible section of the main body and to a respective second anchoring means.

These first and/or second body supports may include first and/or second fixation means which assist in transmitting actuating forces for the extensible body section, i.e., such that these actuating forces convert the extensible body section from its unextended state to its extended state (wherein the extensible body section is lengthened in comparison with its unextended state). "Fixation means" should be understood to be mechanisms which make it possible to secure pushers or other actuation devices on the fastening device with the goal of transferring forces or implementing other interactions between the secured actuation devices and the fastening device. The fixation means on the fastening device may include stops, collars, means for hooking on actuation devices, or any other suitable mechanism.

The fastening device can be provided with a simple design which makes it possible to induce folding of the flexible device on the shaft of the electrode line. This simple design is especially advantageous because this makes it possible to avoid the complex mechanisms known in the prior art. These mechanisms have problems in terms of reliability and imperviousness because of their pivot bearings and/or friction bearings. Furthermore, the fastening device can be manufactured very easily and with fewer manufacturing steps.

In another version of the invention, the main body of the fastening device includes a lumen having an opening in the first end of the main body and extending to the second end, and preferably having another opening in the second end. In another preferred version of the invention, the opening on the first and/or second ends of the main body includes a sealing element, preferably a lip sealing ring. In an especially preferred version, a first fixation means as described above is provided in the second end, and a second fixation means as described above is preferably provided in the opening on the first end.

A lumen is advantageous in conjunction with the invention because this lumen may serve as a drug depot, and/or it may serve to hold electrically active or passive components, thereby ensuring the functionality of the permanently or temporarily implantable device. However, this lumen preferably serves to receive the pusher or other actuation means for operation of the fastening device. The lumen may be provided as a cavity in the interior of the device, and may assume any three-dimensional shape, particularly one which enhances the functionality of the permanently or temporarily implantable device.

The invention also improves upon the electrode lines of the prior art so that the electrode line has a simple design and is suitable for facilitating repositioning and/or explantation. A preferred electrode line includes:

- an elongated shaft having a proximal end and a distal end,
- a fastening device provided at the distal end of the shaft, whereby the first end of the main body is fixedly connected to the distal end of the shaft,
- at least one electrically active surface on the first body support and/or second body support, and
- at least one electric conductor which extends from the proximal end of the shaft beyond the distal end of the shaft as far as the electrically active surfaces.

In the context of the invention, a shaft should be understood to be an elongated structure having a longitudinal axis and preferably a round or elliptical cross section perpendicular to the longitudinal axis. The length measured along the longitudinal axis exceeds a multiple of the major diameter or cross section of the shaft. The shaft preferably includes a flexible and possibly extensible body, preferably having a slidable dielectric layer on the outside. This layer is preferably polyurethane or a polyurethane-silicone copolymer. In addition, the shaft may include at least one stabilizing element in the form of a helical spring situated in the slidable dielectric layer and running concentrically around the longitudinal axis. The spring may also serve as an electric conductor, which at the proximal end is electrically connected to an electrically active implant preferably via a standard plug (e.g. IS-4, DF-1, 15-1). The connection is made in such a way that it electrically conducts signals from the electrically active implant. The electric conductor may also be an independent component.

The elongated shaft-like shape of the main body may be an elongated structure having a longitudinal axis and a round or elliptical cross section perpendicular to the longitudinal axis. The length measured along the longitudinal axis exceeds the transverse axes, which describe the cross section. The shaft includes a flexible and preferably extensible main body which includes a slidable dielectric layer on the outside. The cross section of the shaft-like shape of the main body may have the same shape as the shaft or a different shape.

The advantage of easy repositioning and/or explantation particularly realized with intracardiac electrode lines with passive attachments. The inside wall of the atrium and/or ventricle is lined with the trabecular network. This is a network of mesh-like myocardial tissue. The anchoring means can easily become hooked in this structure. In some cases, serious injuries may occur during explantation and/or repositioning. The folding of the protruding finger-shaped anchors or other anchoring means thus yields a reduction in the risk of injury and facilitates repositioning.

Even more significantly, the improvements of the invention are realized with intracardiac electrode lines that have already been implanted and must be replaced and explanted because of a defect. Such electrode lines are affixed by tissue growth due to natural processes. Thus with traditional electrodes known from the state of the art, a fixed connection is formed between the myocardial tissue and the connecting means of a passive electrode. Such electrodes can no longer be explanted easily in practice. Open heart surgery is unavoidably necessary.

The electrode has the advantage that through the interaction of the change in length of the main body of the fastening device with the folding up of the anchoring means, loosening of the tissue occurs and thus explantation is possible without any great effort by using traditional cardiological means.

In this context, the shaft of the electrode line has a terminal on its proximal end that serves to connect the at least one electric conductor to an electrically active implant. The electric terminal is preferably a plug, which especially preferably corresponds to a standardized plug of the form IS-1 and/or DF-1 or IS-4.

In this context, the electrode line may be characterized by a shaft which also includes a lumen that extends from the proximal end to the distal end of the shaft and forms an opening in the proximal and distal ends, whereby the opening in the distal end and the opening in the main body of the fastening device are connected, such that a guide wire and/or mandrel can be advanced to guide the electrode line and/or to stretch and/or extend the flexible extensible section of the main body of the fastening device.

In this context, the shaft and/or flexible extensible sections of the electrode line have at least one radially stable extensible and/or stretchable stabilizing element, which preferably is designed in the form of a spiral and serves as an electric conductor.

The electrode line may also be characterized in that the flexible extensible section of the main body is surrounded by at least one flexible extensible and/or stretchable insulating sheathing layer, which preferably sheaths the first and/or second body supports at least in some sections and especially preferably also forms the material of the first and/or second anchoring means and/or the first and/or second mechanism for retractions. The section coated with the same extensible material from the first and/or second body support extends around the first and/or second anchor mounts. This section is bordered at the one end by the one end of the first and/or second body support, which is attached to the flexible section. At the other end, this section extends in the direction opposite the aforementioned end to such an extent that the first and/or second anchor mounts are in the coated area.

In addition, the invention may provide a system for simple use of the fastening device. The system may convert the extensible section of the fastening device or electrode line from an unextended state into an extended state which is lengthened in comparison with the unextended state. The system may include first fixation means in the first body support, and a pusher with a first counterstop, such that the counterstop interacts directly with the first fixation means. In one version of the system, the abutting device is a guide wire or mandrel.

In this context, the term "interact" is understood to refer to a transfer of force, among other things, such that the force is exerted by a surgeon on the pusher outside of the body, this force then being transferred either direct or indirectly from this pusher to the fastening device. This force is directed and is of such a magnitude that it acts on the main body of the fastening device, in particular on the extensible and flexible section, so that the latter goes from an unextended state to an extended state which has been stretched in comparison with the unextended state.

The system preferably includes a second counterstop which cooperates directly or indirectly with the second fixation means. In an especially preferred version of the system, the second stop includes clamping means with which the pusher can be affixed with the shaft of the electrode line, and thus enters into indirect interaction via the shaft on the second fixation means to thereby form a support with respect to the interaction of the first counterstop with the first fixation means.

The invention also encompasses a method for moving the first anchoring means in the direction of the main body, by converting the extensible section of the main body of the fastening device (or electrode line) from an unextended state to an extended state which is lengthened in comparison with the unextended state, with the help of the aforementioned system. The method may include the following steps:

bringing the first counterstop of the pusher into direct contact (and thus interaction) with the first fixation means of the first body support;

bringing the second counterstop of the pusher into direct or indirect contact (and thus interaction) with the second attaching means of the second body support;

exerting a force directed away from the second fixation means on the support device, which is transferred to the first fixation means via the first counterstop and deflects the first body support, so that it is moved away from the second body support to convert the extensible section of the main body from an unextended state into an extended state, which is lengthened in comparison with the unextended state.

BRIEF DESCRIPTION OF THE DRAWINGS

The invention is explained in greater detail below on the basis of the following drawings, in which.

DETAILED DESCRIPTION OF PREFERRED VERSIONS OF THE INVENTION

Figure 1:
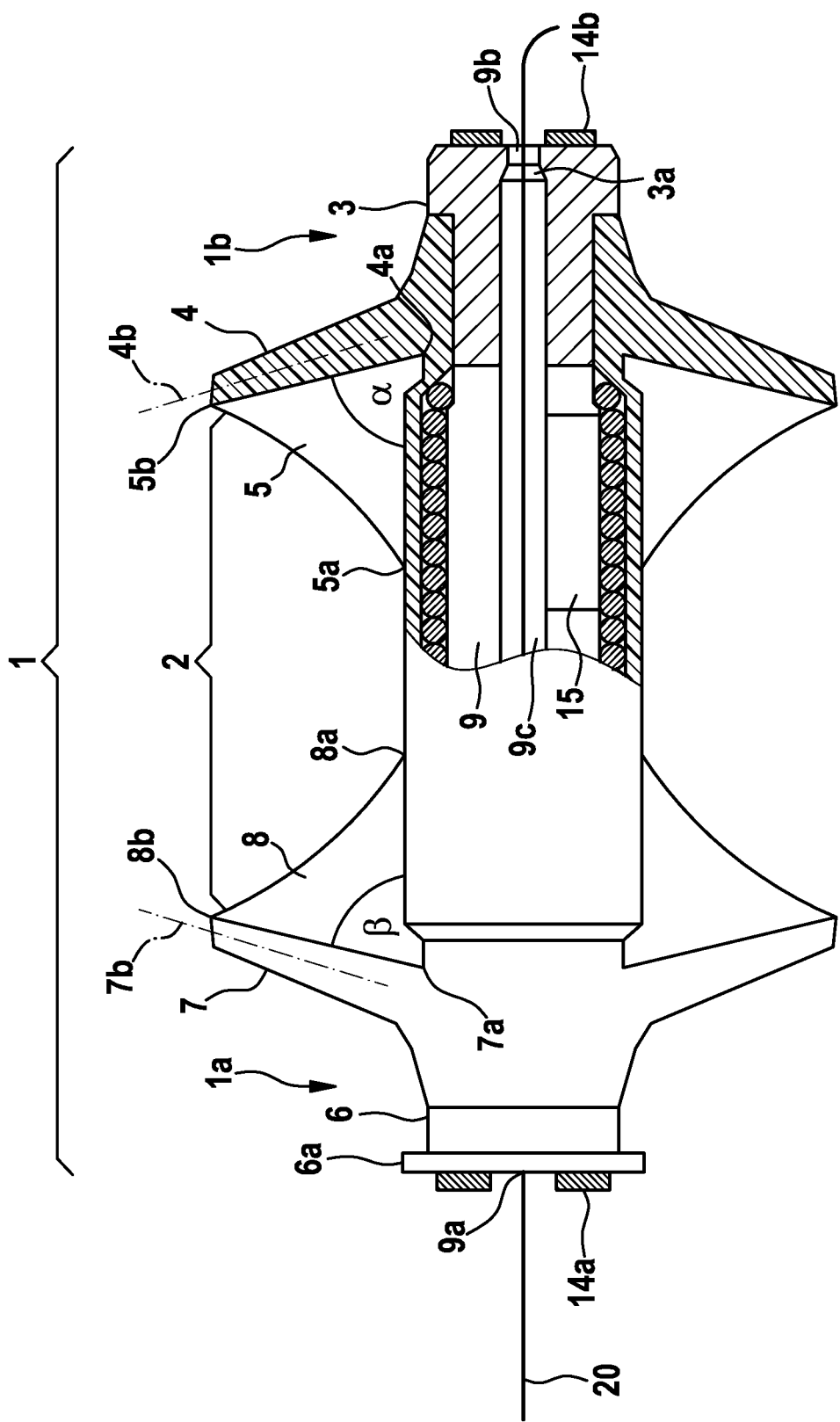
FIG. 1: shows an exemplary version of the fastening device of the invention, partially in cross-section.

FIG. 1 shows an exemplary fastening device having a main body 1 with a first end 1a and a second end 1b. The main body 1 includes an extensible and flexible section 2, a first body support 3 on the second end 1b, a second body support 6 on the first end 1a, and a lumen 9 passing through the main body 1. The lumen 9 forms an opening 9b in the first body support 3 and an opening 9a in the second body support 6. The lumen 9 can accommodate components such as a microelectronic unit for analyzing data from a sensor for blood pressure measurement, a transceiver for data transmission of the data analyzed by the microelectronic unit via far-field or near-field telemetry to a device (not shown here) external to the body, and a power supply. For the sake of simplicity, these components are characterized here collectively as electrically active elements 15. The sensor itself is formed by two sensor elements 14a and 14b on the body supports 6 and 3, which measure the different ambient pressure, for example, and transmit it to the microelectronic unit via electric connections (not shown).

In addition, a guide wire lumen 9c, which seals the electrically active elements 15 with respect to the openings 9a and 9b, is provided in the lumen 9 of the fastening device. A guide wire 20 can be advanced through this guide wire lumen 9c, the guide wire 20 having previously been placed in the body and/or in a vessel or cavity in the body in the location where implantation of the implantable medical device has been provided. Due to the fact that the one end of the guide wire 20 is situated outside of the body, the implantable medical device may be brought to this location on the guide wire 20.

Fixation means 3a and 6a are provided in or on the body supports 3 and 6. In this example, the first fixation means 3a is formed by a shoulder in the opening 9b, while the second fixation means 6a is formed by a collar.

In addition, the device in FIG. 1 has at least one first and at least one second flexible anchoring means (here finger-shaped anchors) 4 and 7, which are attached to the first and second body supports 3 and 6 at anchor mounts 4a and 7a. Both are arranged in such a way that the respective longitudinal axes 4b and 7b of the anchoring means 4 and 7 form a variable angle α and β to the main body 1. The angles are such that the ends of the two anchoring means 4 and 7 spaced away from the main body 1 face toward one another. The anchoring means 4 and 7 are constructed here so that they are prestressed and recoil back into the protruding starting position whenever a force is exerted in the direction of the main body 1. This action can be structurally assisted, for example, by widening the base of each anchoring means 4 and 7, and having the anchoring means 4 and 7 run conically from their anchor mounts 4a and 7a. The anchoring means 4 and 7 fulfill the task of ensuring attachment in the tissue. Preferably one to four of the first and second anchoring means 4 and 7 are distributed about the main body 1 so that they can easily establish anchoring of the implantable medical device. Three of each of the first and second anchoring means 4 and 7 are most preferably provided in each case.

FIG. 1 also shows exemplary first and second flexible retraction devices 5 and 8 for retraction of the respective first and second anchoring means 4 and 7. In this case, the retraction devices 5 and 8 are designed as flexible fins. Each of the flexible fins 5, 8 is attached without interruption to the main body 1 along the segment between the respective body fastening locations 5a, 8a and the anchor mounts 4a, 7a of the respective anchoring means 4, 7, and each of the flexible fins 5, 8 is also attached to the respective first and second anchoring means 4, 7 without interruption between the fastening locations 5b, 8b and the anchor mounts 4a, 7a. The flexible devices 5 and 8 might take the form of membranes designed like the webbing known from amphibians and/or reptiles rather than taking the form of the flexible fins 5, 8.

Figure 2:
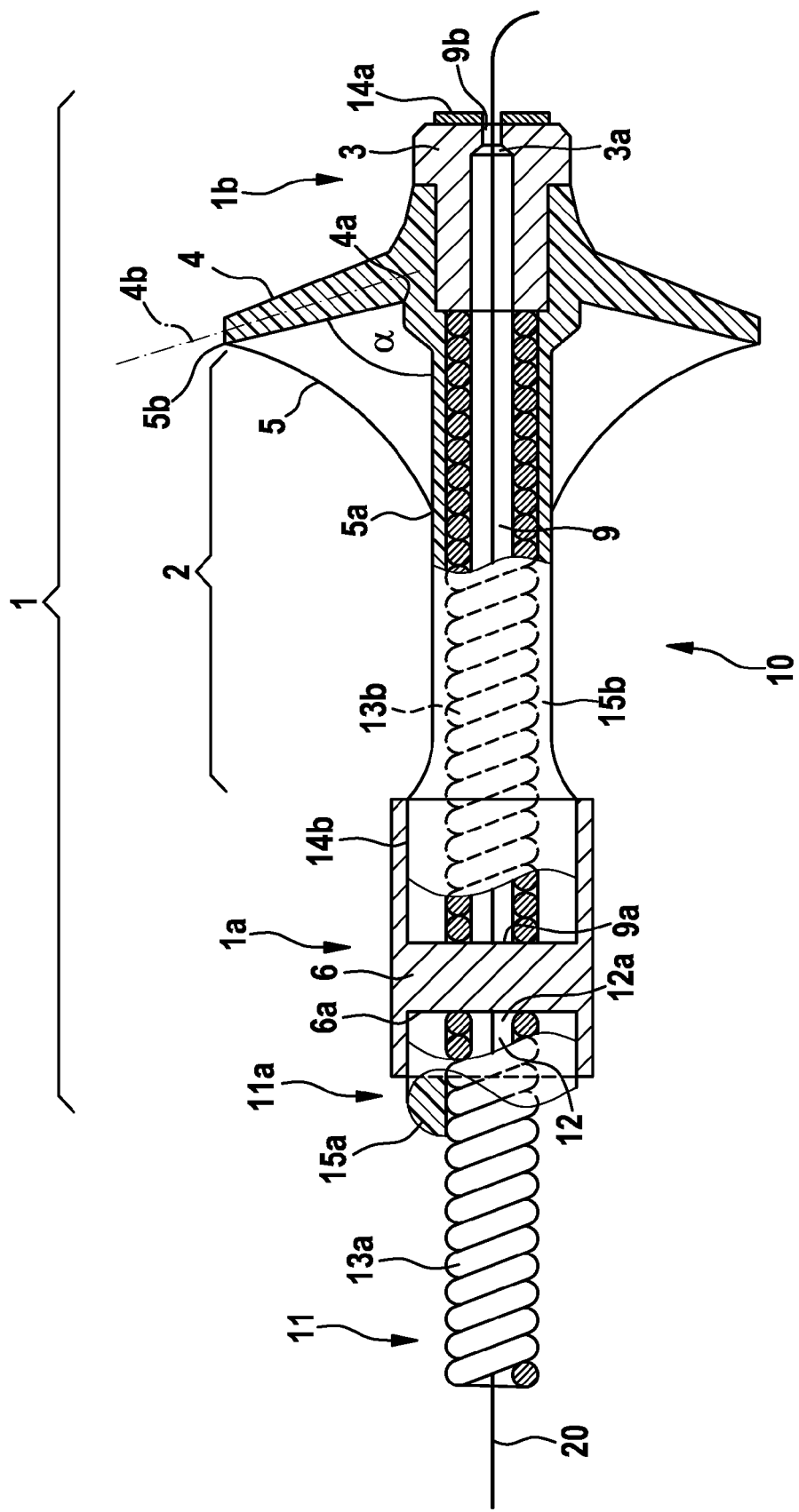
FIG. 2: shows an exemplary version of the electrode line of the invention, partially in cross-section.

FIG. 2 shows an exemplary electrode line 10 having an elongated shaft 11 and an exemplary fastening device. The shaft 11 has a proximal end (not shown) on which a plug contact allows a connection to an electromedical implant. A guide wire lumen 12 passes through the shaft 11 from its proximal end to its distal end 11a. This lumen 12 forms a proximal opening in the plug contact and a distal opening 12a on the distal end 11a of the shaft 11. The wall of the guide wire lumen 12 is formed by inextensible or stretchable stabilizing means 13a, which are stable radially and longitudinally. In the case of the electrode line 10 of FIG. 2, this stabilizing means is a helical spring which runs from the plug connection on the proximal end to the distal end 11a of the shaft 11. The stabilizing means 13a is surrounded by an exterior insulating and slidable layer 15a, which is preferably made of a polymer, especially preferably polyurethane or a polysiloxane copolymer.

The exemplary fastening device is fixedly connected to the distal end 11a of the shaft 11. The fastening device has a main body 1 with a proximal end 1a and a distal end 1b. In addition, the main body 1 has an extensible and flexible section 2, a distal body support 3 on the end 1b, a proximal body support 6 on the proximal end 1a of the main body 1, and a guide wire lumen 9 passing through the fastening device, forming a distal opening 9b in the distal body support 3 and a proximal opening 9a in the proximal body support 6. The proximal opening 9a in the proximal body support 6 is in direct contact with the distal opening 12a of the guide wire lumen 12 of the shaft 11, so that a guide wire 20 can be guided from the proximal end of the shaft 11 through the guide wire lumens 9 and 11 and through the distal opening 9b. The electrode line 10 may thus be guided along a guide wire 20 up to the desired implantation site of the electrode.

The wall of the guide wire lumen 9 is formed by a radially stable but longitudinally extensible and/or stretchable stabilizing means 13b, here formed by a helical spring running from the proximal body support 6 to the distal body support 3. The stabilizing means 13b is surrounded by an exterior insulating and slidable layer 15b, which is also longitudinally extensible and stretchable and is preferably made of a polymer, especially preferably polyurethane or a polysiloxane copolymer.

The helical spring 13b serves at the same time as an electric conductor, which together with the helical spring 13a of the shaft 11 forms an electric conductor. This electric conductor establishes an electric connection between the electromedical device on the proximal end and an electrically active area 14a. The electrically active area 14a serves to deliver a stimulation pulse generated in the electromedical device to the surrounding tissue. The electrically active surface 14a is on the distal body support 3 and has a ring shape around the distal opening 9b, for example. In addition, another electrically active surface 14b may also be provided on the proximal body support 6 to allow bipolar stimulation, for example. In this case, two electric conductors are required, preferably being formed by two mutually insulated and interlooped helical springs, for example.

Fixation means 3a and 6a are provided on the body supports 3 and 6. With the exemplary electrode line from FIG. 2, the fixation means 3a are formed by a shoulder in the opening 9b, while the fixation means 6a are formed by a counterstop in the body support 6, which is directly connected to the shaft 11 and thus force can be applied to the fixation means indirectly from the proximal end.

In addition, the device in FIG. 2 has at least one distal flexible anchoring means (e.g., a finger-shaped anchor) 4 attached to the distal body support 3 at the anchor mount 4a. Each anchoring means 4 is arranged in such a way that the longitudinal axis 4b of the anchoring means 4 forms a variable angle α with the main body 1. The angle α is set so that the end of the anchoring means 4 spaced away from the main body 1 is oriented in the direction of the proximal body support 6. Each anchoring means 4 is constructed and prestressed so that when it receives force in the direction of the main body 1, it folds/recoils into the protruding starting position. This action can be assisted by widening the base of the anchoring means 4 at the anchor mount 4a, and/or by having each anchoring means 4 run conically from the anchor mount 4a in the direction of the end of the anchoring means 4 spaced away from the main body. The anchoring means 4 assists in affixing the fastening device in the tissue. Preferably one to four distal anchoring means 4 are distributed in such a way that anchoring of the implantable medical device can easily be established. Three distal anchoring means 4 are particularly preferred.

Each of the distal anchoring means 4 is connected to a flexible mechanism 5 for retracting the respective distal anchoring means 4. In the exemplary version of FIG. 2, the retraction devices 5 are embodied as flexible fins. Each of the flexible fins 5 are attached to the main body 1 without interruption between a respective body fastening location 5a on the flexible and extensible body section 2 and the anchor mount 4a of the respective distal anchoring means 4, and without interruption between the fastening location 5b on the distal anchoring means 4 and the anchor mount 4a on the respective distal anchoring means 4. Instead of flexible fins, membranes constructed like the webbing known from amphibians and/or reptiles are also possible.

In another version not shown in the drawings, it is also possible to provide anchoring means on the proximal body support 6, with such anchoring means having a shape and effect similar to those of the version from FIG. 1.

FIG. 1 shows a fastening device, and FIG. 2 shows an electrode line having a similar fastening device in a first state. In this first state, the extensible flexible section 2 of the main body 1 is in an unextended state, and thus the fins 5 and 8 are in a relaxed state. Due to the design-related prestress, the flexible finger-shaped anchoring means 4 and 8 protrude outwardly. A permanently or temporarily implantable medical device can be anchored in the tissue of a human body by using such means.

Figure 3:
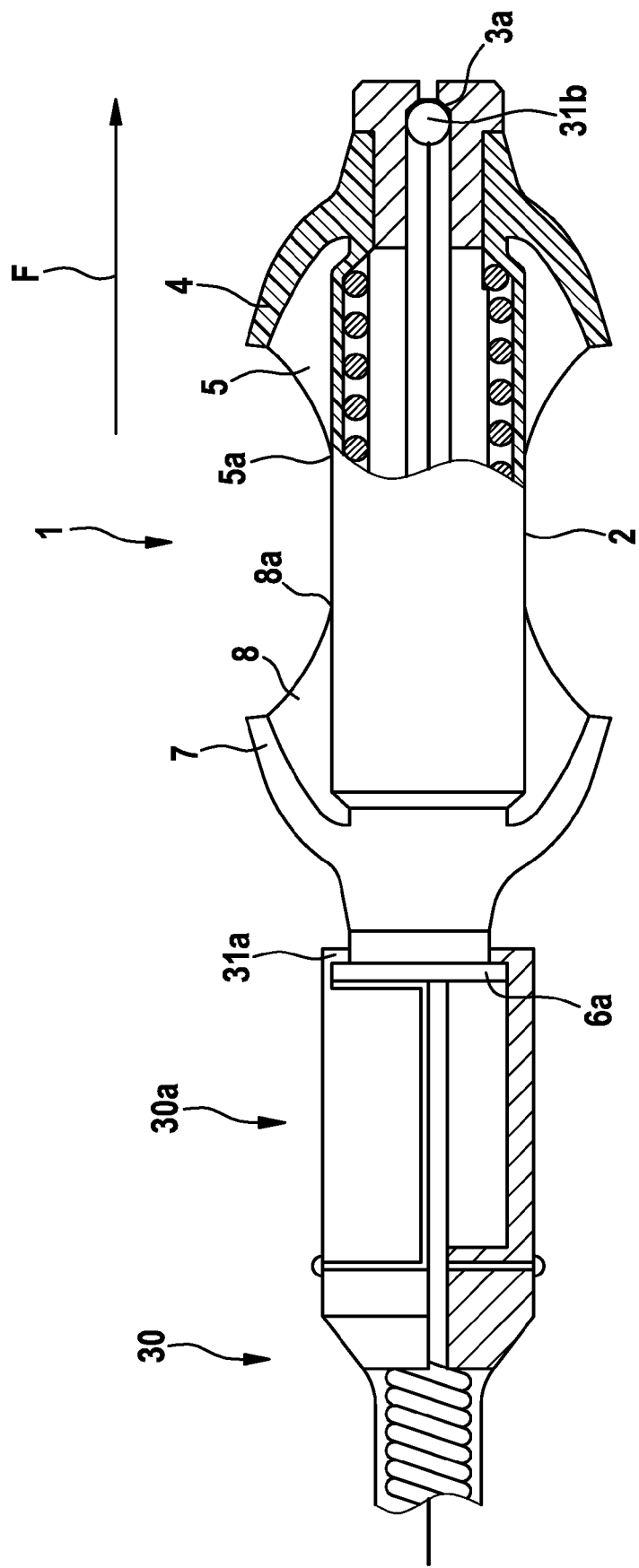
FIG. 3: shows an exemplary version of the system of the invention, in which the fastening device is in an extended state.
Figure 4:
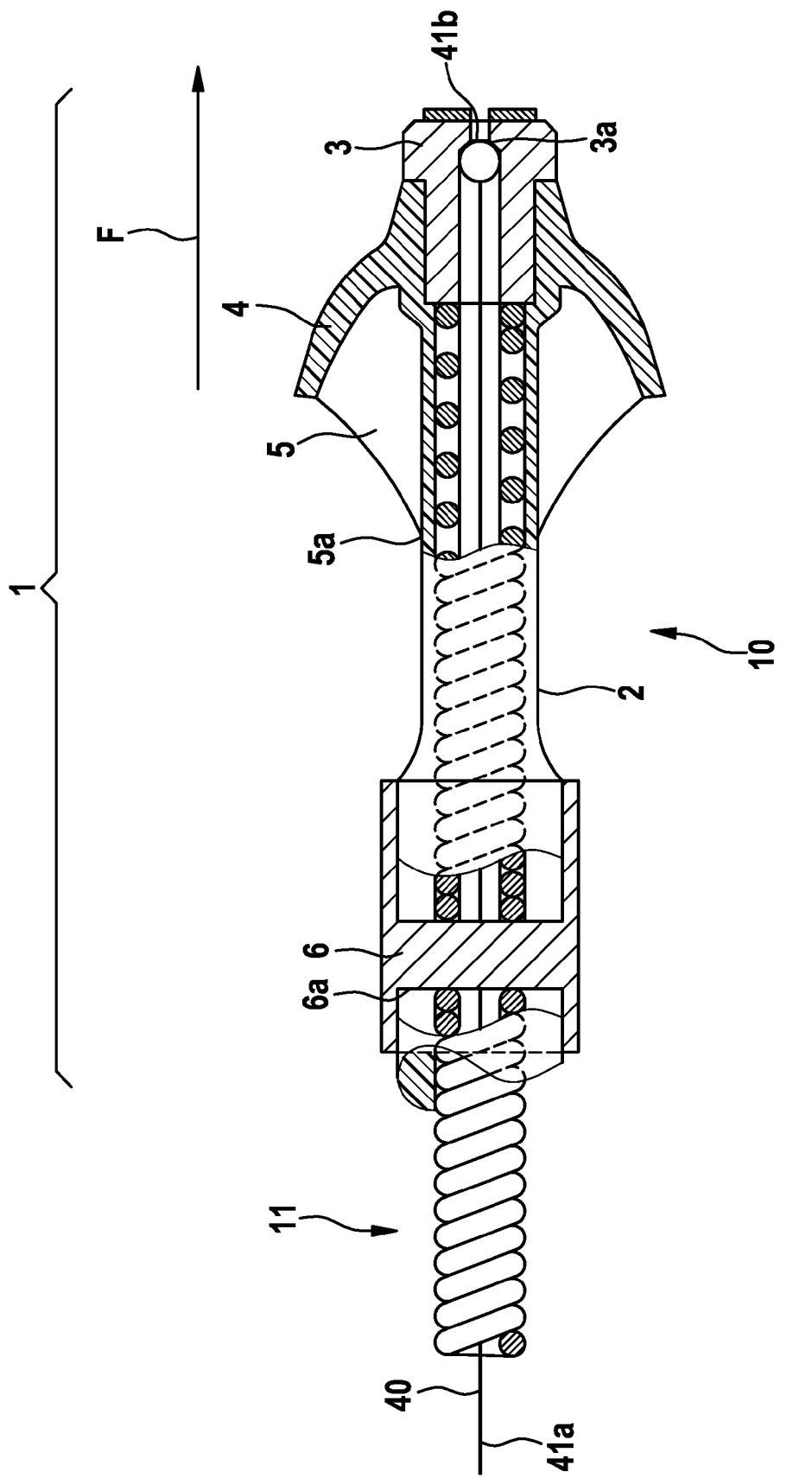
FIG. 4: shows an exemplary version of the system of the invention, in which the extensible and flexible section of the electrode line is in an extended state.

FIGS. 3 and 4 illustrate the functioning of the exemplary fastening device.

FIG. 3 shows an exemplary system for converting the extensible body sections 2 of a fastening device from an unextended state to an extended state, which is lengthened in comparison with the unextended state. The fastening device is identical to that described in FIG. 1, but the electrically active elements are not shown for sake of simplicity.

In addition to the fastening device, FIG. 3 shows a pusher 30, which has a proximal end (not shown) outside of the body and a distal end 30a on which the fastening device is mounted. The fastening device is detachably connected to the pusher via a second counterstop 31a, so that the fastening device together with the pusher 30 can be introduced into the body and can be removed again there. Therefore, the second counterstop 31a in the version shown here is designed as a clamping device and is detachably connected to the second body support 6a, which is shaped as a collar.

In addition, the pusher 30 includes a first counterstop 31b, which is in direct contact with the first fixation means 3a of the fastening device. The first counterstop 31b is attached to a wire that is displaceable with respect to the second counterstop 31a. The first counterstop 31b may be displaced in a direction which leads away from both the proximal end of the pusher 30 and from the second counterstop 31a, and in doing so exerts a force F on the first fixation means 3a, acting in parallel with the direction of movement of the first counterstop 31b and away from the proximal end of the pusher 30 and its second counterstop 31a. At the same time, the second counterstop 31a forms a body support which applies a force acting in the opposite direction from the force acting on the first fixation means 3a. The pusher 30 thus interacts directly with the fastening device via the first counterstop 31b and the second counterstop 31a, so that the force acts directly on the extensible body section 2 and causes it to extend and to be converted to an extended state, which is lengthened in comparison with the unextended state.

The lengthening of the extensible body section 2 also affects the finger-shaped anchoring means 4 and 7. The anchoring means 4 and 7 are fixedly connected to the extensible and flexible section 2 via the flexible retraction devices 5 and 8, which are again shown as fins. Due to the extension of body section 2 in the extended state, wherein the body section 2 is lengthened in comparison with its unextended state, the applied forces acting on the body fastening locations 5a and 8a of the flexible fins 5 and 8 and are thereby transmitted to the finger-shaped anchoring means 4 and 7. In other words, the change in length of the extensible body section 2 is transferred to the anchoring means 4 and 7 via the flexible fins 5 and 8, which results in the anchoring means 4 and 7 being unfolded. This means that the angles α and β, which are greater in the unextended state, are converted to an acute angle when the body section 2 is converted to an extended state, which is lengthened in comparison with the unextended state.

The extended state is achieved when the finger-shaped anchoring elements 4 and 7 flex toward the main body 1. In this state, the position of the counterstop 31*b* can be affixed with respect to the second counterstop 31*a* by acting on the proximal end of the pusher 30 outside of the body. In this way, the fastening device and thus the implantable device can easily be implanted, explanted or repositioned in the body. If a suitable position in the body has been found, the fixation can be released and the force acting on the first fixation means 3*a* decreases, while the extensible flexible body section 2 resumes its original unextended length. The reduction in force acting on the first fixation means 3*a* is also transferred to the flexible fins 5 and 8. In this way, the anchoring means 4 and 7 can recoil into the protruding starting position. In this state, the fastening device and thus the implantable device are anchored. After successful anchoring of the fastening device, the connection to the pusher 30 can be released by releasing the second counterstop 31*a*, which is designed as a releasable clamping device.

FIG. 4 shows an exemplary system wherein the extensible and flexible section of the electrode line 10 is in an extended state. When the extensible and flexible body section 2 of the main body 1 is converted from an unextended state to an extended state which is lengthened in comparison with the unextended state, the flexible retraction devices 5 and the at least one distal anchoring means 4 act as described in the description of FIG. 3.

The pusher 40 for the exemplary electrode line 10 consists of a wire 41*a* with a counterstop 41*b* mounted on its distal end in direct contact with the distal fixation means 3*a* situated in the opening 9*a* of the guide wire lumen 9 in the distal body support 3 of the main body 1, and the wire 41*a* therefore enters directly into interaction with the main body 1. The second counterstop of the pusher 40 is formed by a clamping device (not shown) on the proximal is end of the pusher 40 (also not shown), with the clamping device being situated outside of the patient's body. This clamping device is detachably connected to the plug connection on the proximal end of the electrode line 10 or to the shaft 11. The second counterstop is thus indirectly in contact with the proximal fixation means 6*a* on the proximal body support 6 of the main body 1 and thus interacts indirectly with the main body 1. The effect of the second counterstop as a support can be transmitted indirectly to the proximal fixation means 6*a* via the shaft 11, and the flexible anchoring means 4 can be moved in the direction of the main body by converting the extensible and flexible body section 2 from an unextended state to an extended state that is lengthened in comparison with the unextended state.

It should be understood that the versions of the invention described above are merely exemplary, and the invention is not intended to be limited to these versions. Rather, the scope of rights to the invention is limited only by the claims set out below, and the invention encompasses all different versions that fall literally or equivalently within the scope of these claims.

What is claimed is:

1. A fastening device for fixing implantable medical devices to tissue including:
   a. a main body (1) having:
      (1) a first end (1*a*),
      (2) a second end (1*b*) bearing an inflexible and inextensible first body support (3),
      (3) an extensible body section (2) between the first end (1*a*) and the second end (1*b*),
   b. a flexible elongated first anchor (4):
      (1) extending from the main body (1), and
      (2) being attached to the first body support (3) at a first anchor mount (4*a*), and
   c. a flexible first retraction device (5) connected between a first anchor fastening location (5*b*) on the first anchor (4) and a first body fastening location (5*a*) on the extensible body section (2) of the main body (1), the first retraction device (5):
      (1) serving as a tether on the first anchor (4), whereby tension on the first retraction device (5) is transmitted to the first anchor (4), and
      (2) including a thin flexible fin extending attached without interruption:
         (a) along a length of the first anchor (4) between the first anchor fastening location (5*b*) and the first anchor mount (4*a*), and
         (b) along a length of the extensible body section (2) between the first anchor mount (4*a*) and the first body fastening location (5*a*);
   the extensible body section (2) being convertible from an unextended state into an extended state wherein:
      i. the spacing between the first body fastening location (5*a*) and the first anchor mount (4*a*) is increased, and
      ii. the first anchor (4) is pulled by the first retraction device (5) toward the extensible body section (2).

2. The fastening device of claim 1 wherein the extensible body section (2) includes a helical conductor (13*b*) sheathed within an extensible insulating layer (15*b*).

3. The fastening device of claim 1 wherein the first retraction device (5) is inextensible, such that the distance between the first anchor fastening location (5*b*) on the first anchor (4) and the first body fastening location (5*a*) on the extensible body section (2) does not extend.

4. The fastening device of claim 1 wherein the extensible body section (2) and the first anchor (4) are integrally formed as a unitary part.

5. The fastening device of claim 1 wherein the main body (1) further includes an inflexible and inextensible second body support (6) affixed to the first end (1*a*) of the main body (1).

6. The fastening device of claim 5 further including:
   a. a flexible elongated second anchor (7):
      (1) extending from the main body (1), and
      (2) being attached to the second body support (6) at a second anchor mount (7*a*), and
   b. a flexible second retraction device (8) connected between a second anchor fastening location (8*b*) on the second anchor (7) and a second body fastening location (8*a*) on the extensible body section (2) of the main body (1), the second retraction device (8) serving as a tether on the second anchor (7), whereby tension on the second retraction device (8) is transmitted to the second anchor (7).

7. The fastening device of claim 1 wherein:
   a. the first body support (3) includes a first fixation means (3*a*) for coupling to an object (30/40), wherein force transmitted along the object (30/40) is exerted on the first body support (3) through the first fixation means (3a);
b. the main body (1) includes a body lumen (9) defined therein, the body lumen (9) having a first opening (9a) in the first end (1a) of the main body (1) and having a narrowed throat at the first fixation means (3a);
c. the fastening device further includes a pusher (30, 40) retractably inserted within the body lumen (9), the pusher (30, 40) having an end with a first counterstop (31b, 41b) engaging the first fixation means (3a) at the narrowed throat.

8. The fastening device of claim 1 wherein:
a. the first body support (3) includes a first fixation means (3a) for coupling to an object (30/40), wherein force transmitted along the object (30/40) is exerted on the first body support (3) through the first fixation means (3a);
b. the main body (1) includes a body lumen (9) defined therein, the body lumen (9) having a first opening (9a) in the first end (1a) of the main body (1) and extending to the first fixation means (3a);
b. the fastening device further includes a pusher (30, 40) retractably inserted within the body lumen (9), the pusher (30, 40) having a first counterstop (31b, 41b) which engages the first fixation means (3a).

9. The fastening device of claim 8 wherein:
a. the main body (1) further includes an inflexible and inextensible second body support (6) affixed to the first end (1a) of the main body (1);
b. the second body support (6) includes a second fixation means (6a) for coupling to an object (30/40), wherein force transmitted along the object (30/40) is exerted on the second body support (6) through the fixation means (6a);
c. the pusher (30, 40) includes a second counterstop (31a) which engages the second fixation means (6a).

10. The system of claim 9 wherein the second counterstop (31a) defines a clamp engaging about at least a portion of the second fixation means (6a).

11. The fastening device of claim 8 wherein the body lumen (9) opens upon the first body support (3) of the second end (1b) of the main body (1) at a terminal end of the fastening device.

12. The fastening device of claim 1 wherein:
a. the main body (1) includes a body lumen (9) defined therein, the body lumen (9) having a first opening (9a) in the first end (1a) of the main body (1) and a second opening (9b) at the second end (1b),
b. the anchor (4) extends from the main body (1):
 (1) between the first end (1a) and the second end (1b), and
 (2) situated rearwardly from the second opening (9b).

13. The fastening device of claim 12 wherein the body lumen (9) bears a gasket about its circumference.

14. The fastening device of claim 1 wherein:
a. the main body (1) includes a body lumen (9) extending between a first opening (9a) in the first end (1a) of the main body (1) and a second opening (9b) in the second end (1b) of the main body (1),
b. a first fixation means (3a) is situated within or about the second opening (9b),
c. a second fixation means (6a) is situated within or about the first opening (9a).

15. The fastening device of claim 1 further including:
a. an electrically active surface (14b) on the first body support (3), and
b. an elongated shaft (11) having
 (1) a proximal end,
 (2) an opposing distal end (11a) affixed to the first end (1a) of the main body (1),
 (3) an electric conductor (13a/13b):
  (a) extending from the proximal end of the shaft (11),
  (b) in electrical communication with the electrically active surface (14b), and
  (c) having a shaft lumen (12) extending therein from the proximal end to the distal end (11a) of the shaft (11).

16. The fastening device of claim 15 wherein:
a. the main body (1) includes a body lumen (9) extending from a first opening (9a) in the first end (1a) of the main body (1) toward a second opening (9b) in the second end (1b) of the main body (1),
b. the shaft lumen (12) opens onto the first opening (9a) in the main body (1), thereby allowing a guide wire and/or a mandrel (20) to extend through the shaft (11) and into the main body (1).

17. A fastening device for fixing implantable medical devices to tissue including:
a. a main body (1) having:
 (1) a body section (2) extending between a first end (1a) and a second end (1b), the body section (2) being extensible along an extension direction to increase the spacing between the first end (1a) and the second end (1b),
 (2) a body lumen (9) extending from a first opening (9a) in the first end (1a) of the main body (1) toward the second end (1b) of the main body (1);
b. an elongated first anchor (4) extending from a first anchor mount (4a) on the main body (1), at least a portion of the length of the first anchor (4) being flexible, whereby the first anchor (4) may flex between:
 (1) an unextended state wherein the first anchor (4) is oriented more perpendicular to the extension direction,
 (2) an extended state wherein the first anchor (4) is oriented more parallel to the extension direction,
c. a first tether (5) extending between:
 (1) one or more first anchor fastening locations (5b) on the first anchor (4) spaced from the first anchor mount (4a), and
 (2) one or more first body fastening locations (5a) on the extensible body section (2) spaced from the first anchor mount (4a),
d. a pusher (30, 40) removably and retractably inserted within the first opening (9a) of the body lumen (9), the pusher (30, 40) including:
 (1) a first counterstop (31b, 41b) engaging the main body (1) within the body lumen (9) at a location closer to the second end (1b) of the main body (1) than the first end (1a), and
 (2) a second counterstop (31a) engaging the main body (1) at a location closer to the first end (1a) of the main body (1) than the second end (1b),
 wherein the first counterstop (31b, 41b) and second counterstop (31a) are respaceable with respect to each other along the pusher (30, 40),
wherein extension of the body section (2) flexes the first anchor (4) toward the extended state as the distance between the first body fastening locations (5a) and the first anchor mount (4a) increases.

18. The fastening device of claim 17 wherein the first tether (5) is defined by a thin flexible fin extending without interruption:
  a. along a length of the first anchor (4) between the first anchor fastening location (5b) and the first anchor mount (4a), and
  b. along a length of the extensible body section (2) between the first anchor mount (4a) and the first body fastening location (5a).

19. The fastening device of claim 17:
  a. wherein the first end (1a) of the main body (1) bears an electrically active surface (14b);
  b. further including an electrical conductor (13a/13b) extending from the second end (1b) of the main body (1), the electrical conductor (13a/13b) being:
    (1) in electrical communication with the electrically active surface (14b),
    (2) at least partially defined by a spring winding helically along the main body (1).

20. The fastening device of claim 17 further including:
  a. an elongated second anchor (7) extending from a second anchor mount (7a) on the main body (1), at least a portion of the length of the second anchor (7) being flexible, whereby the second anchor (7) may flex between:
    (1) an unextended state wherein the second anchor (7) is oriented more perpendicular to the extension direction,
    (2) an extended state wherein the second anchor (7) is oriented more parallel to the extension direction,
  b. a second tether (8) extending between:
    (1) one or more second anchor fastening locations (8b) on the second anchor (7) spaced from the second anchor mount (7a), and
    (2) one or more second body fastening locations (8a) on the extensible body section (2) spaced from the second anchor mount (7a),
  wherein extension of the body section (2) flexes the second anchor (7) toward the extended state as the distance between the second body fastening locations (8a) and the second anchor mount (7a) increases.

21. The fastening device of claim 17 wherein:
  a. the body lumen (9) includes a second opening (9b) in the second end (1b) of the main body (1), and
  b. the second end (1b) of the main body (1) defines a terminal end of the fastening device.

22. The fastening device of claim 17 wherein the body lumen (9) narrows adjacent the second opening (9b) in the second end (1b) of the main body (1).

23. The fastening device of claim 17 wherein the first counterstop (31b, 41b) of the pusher (30, 40) engages the main body (1) within the body lumen (9) at a narrowing of the body lumen (9) adjacent the second opening (9b) in the second end (1b) of the main body (1).

* * * * *